(12) United States Patent
Kim et al.

(10) Patent No.: US 11,504,113 B2
(45) Date of Patent: Nov. 22, 2022

(54) SUTURE FOR LIFTING AND MANUFACTURING METHOD THEREOF

(71) Applicant: DONGBANG MEDICAL CO., LTD., Chungcheongnam-do (KR)

(72) Inventors: Jung Gwon Kim, Seoul (KR); Keun Shik Kim, Chungcheongnam-do (KR); Eun A Lee, Gyeonggi-do (KR)

(73) Assignee: DONGBANG MEDICAL CO., LTD., Chungcheongnam-do (KR)

( * ) Notice: Subject to any disclaimer, the term of this patent is extended or adjusted under 35 U.S.C. 154(b) by 258 days.

(21) Appl. No.: 16/315,371

(22) PCT Filed: Jul. 7, 2017

(86) PCT No.: PCT/KR2017/007313
§ 371 (c)(1),
(2) Date: Jan. 4, 2019

(87) PCT Pub. No.: WO2018/009031
PCT Pub. Date: Jan. 11, 2018

(65) Prior Publication Data
US 2019/0231351 A1    Aug. 1, 2019

(30) Foreign Application Priority Data

Jul. 8, 2016 (KR) .................. 10-2016-0086525
Jun. 5, 2017 (KR) .................. 10-2017-0069636

(51) Int. Cl.
*A61B 17/06* (2006.01)
*B29C 45/18* (2006.01)
(Continued)

(52) U.S. Cl.
CPC ........ *A61B 17/06166* (2013.01); *A61B 17/00* (2013.01); *A61B 17/04* (2013.01);
(Continued)

(58) Field of Classification Search
CPC .... A61B 2017/06176; A61B 17/06166; A61B 2017/00526; A61B 2017/06057;
(Continued)

(56) References Cited

U.S. PATENT DOCUMENTS 5,669,935 A    9/1997  Rosenman
7,468,068 B2   12/2008 Kolster
(Continued)

FOREIGN PATENT DOCUMENTS

EP    2190358 A1    6/2010
EP    2774579 A1    9/2014
(Continued)

OTHER PUBLICATIONS

English machine translation from the KIPRIS website for KR-10-2016-0066831 (Year: 2016).*
(Continued)

*Primary Examiner* — Katherine M Shi
(74) *Attorney, Agent, or Firm* — Meunier Carlin & Curfman LLC

(57) ABSTRACT

A suture for lifting is disclosed. The suture comprises: a medical fiber yarn; fixing parts formed at one side of the fiber yarn and fixable to the skin; and anchor parts protruding on an outer circumference of the fixing parts, wherein the anchor parts are integrally formed with the fiber yarn by a double injection.

13 Claims, 14 Drawing Sheets

(51) Int. Cl.
*A61L 17/10* (2006.01)
*A61B 17/00* (2006.01)
*D02J 3/02* (2006.01)
*A61F 2/00* (2006.01)
*A61B 17/04* (2006.01)
*A61L 17/14* (2006.01)
*B29C 45/14* (2006.01)
*B29C 45/16* (2006.01)
*B29K 67/00* (2006.01)
*B29L 31/00* (2006.01)

(52) U.S. Cl.
CPC ............... *A61B 17/06* (2013.01); *A61F 2/00* (2013.01); *A61L 17/10* (2013.01); *A61L 17/14* (2013.01); *B29C 45/14336* (2013.01); *B29C 45/14786* (2013.01); *B29C 45/1671* (2013.01); *B29C 45/18* (2013.01); *B29C 45/1866* (2013.01); *D02J 3/02* (2013.01); *A61B 2017/00004* (2013.01); *A61B 2017/00526* (2013.01); *A61B 2017/06176* (2013.01); *A61L 2430/30* (2013.01); *B29K 2067/043* (2013.01); *B29K 2067/046* (2013.01); *B29K 2713/00* (2013.01); *B29K 2995/006* (2013.01); *B29L 2031/753* (2013.01)

(58) Field of Classification Search
CPC ............ A61B 17/06; A61B 2017/0464; A61F 2/0063; A61F 2220/0016; A61F 2002/0068; A61F 2240/001
See application file for complete search history.

(56) References Cited

U.S. PATENT DOCUMENTS

| | | | |
|---|---|---|---|
| 7,582,105 B2 | 9/2009 | Kolster | |
| 8,454,653 B2 | 6/2013 | Hadba et al. | |
| 8,721,666 B2 | 5/2014 | Schroeder et al. | |
| 8,721,681 B2 | 5/2014 | Ruff | |
| 8,932,329 B2 | 1/2015 | Hadba et al. | |
| 2003/0149447 A1* | 8/2003 | Morency | A61B 17/06166 606/228 |
| 2004/0088003 A1 | 5/2004 | Leung et al. | |
| 2005/0267532 A1 | 12/2005 | Wu | |
| 2006/0135995 A1 | 6/2006 | Ruff | |
| 2006/0131116 A1 | 7/2006 | Sander et al. | |
| 2006/0161160 A1 | 7/2006 | Sander et al. | |
| 2007/0038249 A1* | 2/2007 | Kolster | A61B 17/06166 606/228 |
| 2007/0257395 A1 | 11/2007 | Lindh et al. | |
| 2008/0221618 A1* | 9/2008 | Chen | A61B 17/06166 606/228 |
| 2009/0082791 A1 | 3/2009 | Schroeder et al. | |
| 2009/0182375 A1 | 7/2009 | Isse et al. | |
| 2009/0248066 A1* | 10/2009 | Wilkie | A61B 17/06166 606/228 |
| 2009/0312791 A1 | 12/2009 | Lindh et al. | |
| 2010/0211098 A1 | 8/2010 | Hadba et al. | |
| 2011/0288583 A1* | 11/2011 | Goraltchouk | A61B 17/08 606/228 |
| 2012/0150194 A1 | 6/2012 | Odermatt et al. | |
| 2013/0231702 A1 | 9/2013 | Hadba et al. | |
| 2016/0106423 A1* | 4/2016 | Dumanian | A61L 17/00 606/230 |
| 2019/0046184 A1* | 2/2019 | Jung | A61L 33/06 |
| 2019/0231351 A1* | 8/2019 | Kim | A61F 2/00 |

FOREIGN PATENT DOCUMENTS

| | | | |
|---|---|---|---|
| JP | 2002192553 A | 7/2002 | |
| JP | 2010500102 A | 1/2010 | |
| JP | 201194236 A | 10/2011 | |
| JP | 2011194236 A | 10/2011 | |
| KR | 10-2009-0035692 A | 4/2009 | |
| KR | 10-1172829 B1 | 8/2012 | |
| KR | 10-1432497 B1 | 8/2014 | |
| KR | 10-2016-0066831 A | 6/2016 | |
| KR | 101701434 B1 | 2/2017 | |
| KR | 10-2016-0086525 A | 1/2018 | |
| KR | 10-2018-0006012 | 1/2018 | |
| KR | 10-2016-0086525 B1 | 9/2018 | |
| KR | 10-2017-0069636 | 12/2018 | |
| RU | 2528077 C2 | 6/2013 | |
| WO | 2008020937 A2 | 2/2008 | |
| WO | 2010051506 A1 | 5/2010 | |
| WO | 2013016306 A1 | 1/2013 | |
| WO | 2018009031 A1 | 1/2018 | |

OTHER PUBLICATIONS

Office Action for Japanese Application No. 2018-569072. Japanese Patent Office (JPO), dated Nov. 19, 2019.
Office Action for Russian Application No. 20149102549/14(004544). Federal Institute of Industrial Property (FIPS), dated Dec. 12, 2019.
Search Report for Russian Application No. 20149102549/14(004544). Federal Institute of Industrial Property (FIPS), dated Aug. 9, 2019.
Office Action for Russian Application No. 20149102549/14(004544). Federal Institute of Industrial Property (FIPS), dated Aug. 12, 2019.
International Search Report for PCT/KR2017/007313 dated Oct. 13, 2017.
International Search Report for PCT/KR2017/007313 dated Oct. 13, 2017 (English Translation).
KR 10-2017-0069636 Administrative Actions, Decision to Grant Registration. KIPRIS, dated Jan. 31, 2019.
Abstract of KR 101701434B1, KR 101701434B1 Bibliographic Data: KR 101701434 (B1)—Feb. 13, 2017. https://worldwide.espacenet.com/publicationDetails/biblio?CC=KR&NR=101701434B1&KC=B1&FT=D#.
Chinese Office Action received in connection with Chinese patent application No. 201780042077.7, dated Apr. 2, 2020, 11 pages.
Partial supplementary ESR received in connection with European patent application No. 17824587.4, dated Mar. 20, 2020, 12 pages.
Extended European Search Report received in connection with European patent application No. 17824587.4, dated Jul. 10, 2020, 11 pages.
Canadian Office Action received in connection with Canadian patent application No. 3029530, dated Aug. 18, 2020, 4 pages.

\* cited by examiner

SUTURE FOR LIFTING AND MANUFACTURING METHOD THEREOF

PRIORITY

This application is a National Phase conversion under 35 USC 371 of and claims priority to PCT/KR2017/007313, filed Jul. 7, 2017.

TECHNICAL FIELD

The present invention relates to a suture for lifting and a manufacturing method therefor, and more particularly, to a suture for lifting, which can greatly improve the quality and reliability, and a manufacturing method therefor.

BACKGROUND ART

Autogeous materials are present in fibers constituting muscles of a human body. If a foreign substance invades the muscle, autogenous materials gather around the invaded foreign substance to protect the muscle against the invaded foreign substance. The autogenous materials are generated to protect the muscle, consequently strengthening the muscle.

There are numerous kinds of autogenous material. The autogenous material is a chemical factor that is released from artificially wounded tissue cells of some skin muscle tissues and brings about a series of physiological changes to the tissues to provide wound recovery conditions, which will be described below in more detail based on principles of electrobiology, piezoelectric science and general biological control theory. The chemical factor is converted into heat energy to dilate tiny blood vessels and to accelerate lymph circulation, which significantly increases the metabolic rate and enhances nutritional supplement for the wounded part, removes excrescent products through circulation of body fluids while promoting proteolysis of some tissues and increasing peripheral nerve transmitters, and reduce amounts of peptides and 5-hydroxylamine in serum by generating active materials in vascular nerves. Accordingly, information for neuronal regeneration or modulation of the wounded part is delivered to the central nervous system and combining specific biochemical materials present in the human body is expedited to provide effects of increasing human immune functions through facilitated circulation of body fluids, regulating organ functions in the human body and strengthening the muscle.

Technical Problems to be Solved

The present invention provides a suture for lifting, which induces the generation of an autogenous material by easily and simply inserting a medical thread intramuscularly.

The present invention also provides a suture for lifting, the suture including a fiber yarn, anchor parts, fixing parts, and variable parts.

The present invention also provides a suture for lifting, in which a fiber yarn and anchor parts are integrally formed by a double injection process or by multiple injections using two or more of injection stages.

The present invention also provides a suture for lifting, in which a fiber yarn and anchor parts are integrally formed by a double injection process or by multiple injections of two or more of injection stages, thereby improving a tensile strength of the suture.

The present invention also provides a suture for lifting, which can form anchor parts in diverse shapes by a double injection process or by multiple injections using two or more injection stages.

The present invention also provides a suture for lifting, which is made of a biodegradable polymer material that is hydrolyzed in the skin and then eliminated within a predetermined period.

The present invention also provides a suture for lifting, which can improve a cell regenerating effect and biocompatibility by coating collagen on the suture.

The present invention also provides a suture for lifting, which has enhanced flexibility by forming the suture or the fiber yarn into a mesh type.

The present invention also provides a suture for lifting, which allows an autogenous material to easily gather by forming the suture or a fiber yarn into a mesh type.

Accordingly, since the quality and reliability of the lifting suture can be greatly improved, the present invention also provides a suture for lifting and a manufacturing method therefor, which can fulfill a wide variety of consumer needs, thereby giving users favorable product image.

Technical Solutions

In accordance with an aspect of the present invention, there is provided a suture for lifting according to an embodiment of the present invention, the lifting suture including a medical fiber yarn, fixing parts formed at one side of the fiber yarn and fixable to the skin, and anchor parts protruding on the outer circumference of the fixing parts, wherein the anchor parts are integrally formed with the fiber yarn by a double injection.

In one embodiment, the suture may further include variable parts movably or fixably formed at the other side of the fiber yarn and laterally symmetrical with the fixing parts, and anchor parts protruding on the outer circumference of the variable parts, wherein the anchor parts are integrally formed with the fiber yarn.

In one embodiment, the anchor parts may be integrally formed with the fiber yarn by a double injection.

In another embodiment, the anchor parts may be formed one by one at regular intervals so as to expose the fiber yarn in regions enwrapped by the anchor parts to the outside or outside portion of the suture itself.

In still another embodiment, the anchor parts may be formed in bundles with neighboring anchor parts so as not to expose the fiber yarn in regions enwrapped by the anchor parts to the outside or outer portion of the suture itself.

In still another embodiment, the fiber yarn may be injection-molded into a mesh type form.

In still another embodiment, the suture may further include a mesh connector part injection-molded in a mesh type form, the mesh connector part connected between the anchor parts of the fixing parts and the anchor parts of the variable parts and covering the fiber yarn.

In still another embodiment, the mesh connector part may be integrally formed with the fiber yarn together with the anchor parts by a double injection.

In one embodiment, the anchor parts may be made of a material that is the same with or different from a fiber yarn material, wherein the anchor parts include funnel-shaped, symmetric V-grooves integrally formed with the fiber yarn at their first ends along the outer circumference of the fiber yarn by a double injection to provide a locking mechanism capable of a locking operation.

In another embodiment, the fiber yarn may include recesses located to correspond to the anchor parts, and the anchor parts may be integrally formed by injecting an anchor part material into the recesses.

In another embodiment, the fiber yarn may include holes located to correspond to the anchor parts, and the anchor parts may integrally formed by injecting an anchor part material into the holes.

Preferably, the suture is made of a biodegradable polymer material that is hydrolyzed in the skin and then eliminated within a predetermined period, and the biodegradable polymer material may be one selected from the group consisting of polylactic acid (PLA), polydioxanone (PDO) and polyglycolicacide (PGA).

In accordance with another aspect of the present invention, there is provided a manufacturing method for a suture made of a biodegradable polymer material, the manufacturing method including injecting a medical fiber yarn material into a first injection device; injecting an anchor part material that is the same with or different from the fiber yarn material into a second injection device; and integrally forming anchor parts protruding on the outer circumference of a fiber yarn with the fiber yarn by performing one-time molding by a double injection, wherein the double injection is performed such that fixing parts fixable to the skin are formed at one side of the fiber yarn by the anchor parts.

In one embodiment, in the double injection, the anchor parts protruding on the outer circumference of the fiber yarn are integrally formed with the fiber yarn by performing one-time molding by the double injection, wherein the fixing parts fixable to the skin are formed at one side of the fiber yarn by the anchor parts, and variable parts are movably or fixably formed at the other side of the fiber yarn to be laterally symmetrical with the fixing parts by the anchor parts.

In another embodiment, in the double injection, the anchor parts of the fixing parts and the variable parts may be formed one by one at regular intervals so as to expose the fiber yarn in regions enwrapped by the anchor parts to the outside.

In another embodiment, in the double injection, the anchor parts of the fixing parts and the variable parts may be formed in bundles with neighboring anchor parts so as not to expose the fiber yarn in regions enwrapped by the anchor parts to the outside.

In another embodiment, in the double injection, the fiber yarn may be injection molded in a mesh type.

In another embodiment, in the double injection, a mesh connector part may be injection-molded into a mesh type form, the mesh connector part connected between the anchor parts of the fixing parts and the anchor parts of the variable parts and covering the fiber yarn.

In another embodiment, the step of injecting the medical fiber yarn material into the first injection device may be performed after forming recesses or holes in the fiber yarn, and the double injection may include a step of integrally forming the anchor parts by a double injection by injecting the anchor part materials into the recesses or holes.

Preferably, the biodegradable polymer material is one selected from the group consisting of poly lactic acid (PLA), polydioxanone (PDO) and polyglycolicacide (PGA), or collagen having a cell regenerating effect and biocompatibility.

Advantageous Effects

As described above, in the lifting suture according to an embodiment of the present invention, the suture includes a fiber yarn, anchor parts, fixing parts, and variable parts. In the lifting suture according to an embodiment of the present invention, a fiber yarn and anchor parts of the suture are integrally formed by a double injection or by multiple injections including two or more injection stages.

In the lifting suture according to an embodiment of the present invention, a tensile strength of the suture can be improved by integrally forming the fiber yarn and the anchor parts by a double injection or by multiple injections during two or more injection stages.

In the lifting suture according to an embodiment of the present invention, anchor parts can be formed into diverse shapes by a double injection or by multiple injections of two or more injection stages.

In the lifting suture according to an embodiment of the present invention, the suture is made of a biodegradable polymer material that is hydrolyzed in the skin and then eliminated within a predetermined period to ensure accomplishing the required task(s).

In the lifting suture according to an embodiment of the present invention, a cell regenerating effect and biocompatibility can be improved by coating collagen on the suture. In the lifting suture according to an embodiment of the present invention, the suture has flexibility by forming the suture or the fiber yarn into a mesh type form.

In the lifting suture according to an embodiment of the present invention, an autogenous material is allowed to easily gather by forming the suture or the fiber yarn into a mesh type form.

In the lifting suture according to an embodiment of the present invention, since the suture is in a mesh type formed suture, it can be easily manufactured and a medical fluid can be efficiently injected.

Accordingly, the quality and reliability can be greatly improved to fulfill a wide variety of consumer needs, thereby giving users a favorable image of the product.

Preferred embodiments of the present invention for achieving these effects will now be more fully described by reference to the following description, taken in conjunction with the accompanying drawings.

DETAILED DESCRIPTION OF THE DRAWINGS

Figure 1A:
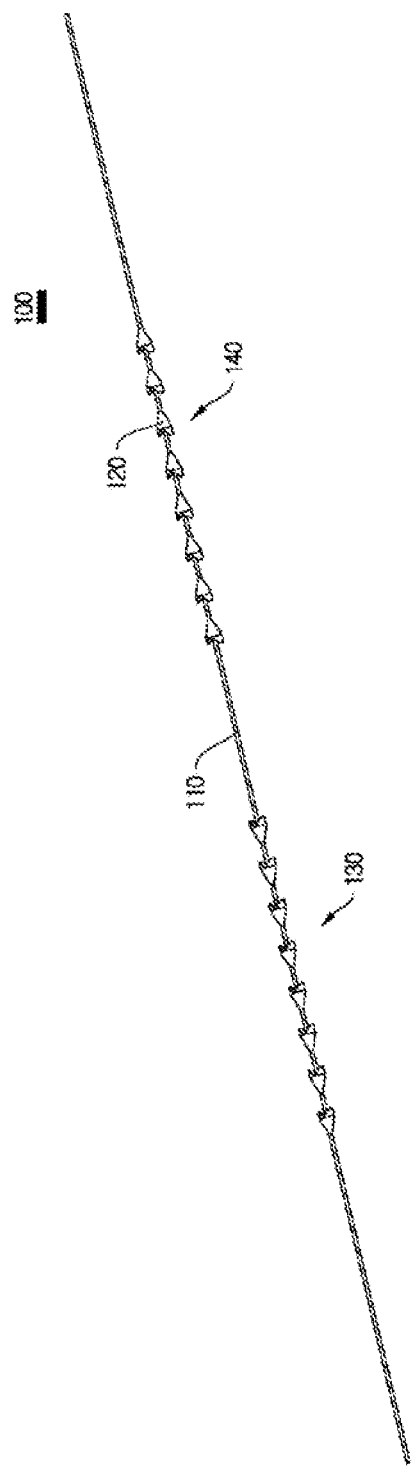
FIG. 1A is a perspective view of a lifting suture (100) according to a first embodiment of the present invention. In the top row of FIG. 1B, the lifting suture (100) is shown in a first orientation of a front view, and in the bottom row, the lifting suture (100) is shown in a second orientation of the front view rotated 90 degrees from the first orientation.

The above and other objects, features and advantages of the present invention will become more apparent by describing in detail preferred embodiments thereof with reference to the attached drawings. Embodiments of the present invention will now be described in detail with reference to the accompanying drawings.

It should be obvious to those of ordinary skill in the art that descriptions including exemplary embodiments of this disclosure have various applications. Therefore, arbitrary embodiments described in the detailed description of the present invention are provided only for better describing the present invention and it is not intended that the scope of the present invention is limited to those embodiments.

The functional blocks shown and described below are provided as possible implementation examples only. Other functional blocks can be used in other implementation examples without departing the spirit and scope of the detailed description of the present invention. In addition, one or more functions blocks of the present invention are represented by individual blocks, but the one or more functional blocks may be combinations of various hardware and software components performing the same function.

In addition, it will be understood that the expression that an element comprises other elements, which is an open expression, when used in this specification, simply specifies the presence of stated elements, but do not preclude the presence or addition of one or more other elements.

Further, it will be understood that when an element is referred to as being connected to another element, it can be directly connected to the other element or intervening elements may be present.

In addition, it will be understood that, although the terms first, second, etc. may be used herein to describe various elements, these elements should not be limited by these terms. These terms are only used to distinguish one element from another element but not to define the order among multiple elements or other features.

Hereinafter, lifting sutures according to various embodiments of the present invention and manufacturing methods therefor will be described.

As used herein, the term "lifting" refers to makeup lifting of wrinkles due to skin aging to keep the skin elastic and taut. Specifically, lifting refers to a skincare for treating fine wrinkles and flaccid and loose skin, which are evidences of skin aging. In lifting, drooping muscles are uplifted and pores are contracted by allowing ultrasonic waves or ions to penetrate into the skin, thereby retaining skin tissues, recovering skin elasticity and lessening the appearance of wrinkles.

In addition, the term "suture" refers to a thread used in closing or binding together human tissue wounds due to surgery or injury. There are a non-absorbable type and an absorbable type, and examples of the former type include silk, nylon, polyterephthalethylene, and so on, and examples of the latter type include catgut, polyglycolic acid, and so on. Particularly, a biodegradable suture is a surgical thread developed to be degraded in the human body. Therefore, a separate step of removing stitches of the biodegradable suture is not required after the surgery.

First, sutures 100, 200 and 300 according to first, second and third embodiments of the present invention are configured as shown in FIGS. 1 to 3, respectively.

The sutures 100, 200 and 300 applied to the present invention include fixing parts 130, 230 and 330 each formed at one side and fixable to the skin, and variable parts 140, 240 and 340 each movably and fixably formed at the other side and laterally symmetrical with respect to the fixing parts 130, 230 and 330, respectively.

Of course, only one among the fixing parts 130, 230 and 330 and the variable parts 140, 240 and 340 applied to the present invention can be formed at only one of opposite sides of each suture.

In addition, the fixing parts 130, 230 and 330 and the variable parts 140, 240 and 340 applied to the present invention are configured such that anchor parts 120, 220 and 320 protruding on outer circumferences of the fiber yarns 110, 210 and 310 are integrally formed with the fiber yarns 110, 210 and 310 by a double injection, respectively.

In addition, the anchor parts 120, 220 and 320 of the fixing parts 130, 230 and 330 and the variable parts 140, 240 and 340 applied to the present invention provide the lifting suture in which the anchor parts 120, 220 and 320 are formed one by one at regular intervals so as to expose the fiber yarns 110, 210 and 310 in regions enwrapped by the anchor parts 120, 220 and 320 to the outer portion of the suture(s), respectively.

In the lifting suture 100 according to the first embodiment of the present invention, the anchor parts 120 are made of the same material with or a different material from the fiber yarn 110, wherein the anchor parts 120 include locking portions 122 which each define funnel-shaped, symmetric V-grooves 124 integrally formed with the fiber yarn_110 at their first ends along the outer circumference of the fiber yarn 110 by a double injection to effectuate a locking operation.

Together with features of the lifting suture 100 according to the first embodiment of the present invention, the lifting suture 200 according to the second embodiment of the present invention is featured in that after forming recesses 250 in the fiber yarn 210, anchor part materials are injected into the recesses 250, thereby integrally forming the anchor parts 220 with the fiber yarn 210 in a closely packed manner.

Together with features of the lifting suture 100 according to the first embodiment of the present invention, the lifting suture 300 according to the third embodiment of the present invention is featured in that after forming holes 260 in the fiber yarn 310, anchor part materials are preferably input to the holes 260, thereby integrally forming the anchor parts 320 with the fiber yarn 310 in a closely packed manner.

Meanwhile, sutures 400, 500 and 600 according to fourth, fifth and sixth embodiments of the present invention are configured as shown in FIGS. 4 to 6, respectively.

The sutures 400, 500 and 600 applied to the present invention include fixing parts 430, 530 and 630 each formed at one side and fixable to the skin, and variable parts 440, 540 and 640 each movably and fixably formed at the other side and laterally symmetrical with respect to the fixing parts 430, 530 and 630, respectively.

Of course, only one among the fixing parts 430, 530 and 630 and the variable parts 440, 540 and 640 applied to the present invention can be formed at only one of opposite sides of each suture.

In addition, the fixing parts 430, 530 and 630 and the variable parts 440, 540 and 640 applied to the present invention are configured such that anchor parts 420, 520 and 620 protruding on outer circumferences of the fiber yarns 410, 510 and 610 are integrally formed with the fiber yarns 410, 510 and 610 by a double injection, respectively.

In addition, the anchor parts 420, 520 and 620 of the fixing parts 430, 530 and 630 and the variable parts 440, 540 and 640 applied to the present invention provide the lifting sutures in which the anchor parts 420, 520 and 620 are formed in bundles at regular intervals by connector parts 470, 570 and 670 so as not to expose the fiber yarns 410, 510 and 610 in regions enwrapped by the anchor parts 420, 520 and 620 to the outside, respectively.

That is to say, in the lifting suture 400 according to the fourth embodiment of the present invention, the anchor parts 420 are made of the same material with or a different material from the fiber yarn 410, wherein the anchor parts 420 include funnel-shaped, symmetric V-grooves integrally formed with the fiber yarn 410 at their first ends along the outer circumference of the fiber yarn 410 by a double injection to effectuate a locking operation. In addition, since the anchor parts 420 of the fixing parts 430 and the variable parts 440 and neighboring anchor parts 420 are connected by the connector part 470 covering the fiber yarn 410 in the fixing parts 430 and the variable parts 440, the anchor parts 420 are formed in bundles at regular intervals so as not to expose the fiber yarn 410 in regions where the anchor parts 420 are formed to the outside or outside portion of the suture by the connector part 470.

Together with features of the lifting suture 400 according to the fourth embodiment of the present invention, the lifting suture 500 according to the fifth embodiment of the present invention is featured in that after forming recesses 550 in the fiber yarn 510, anchor part materials are injected into the recesses 550, thereby integrally forming the anchor parts 520 with the fiber yarn 510 in a closely packed manner.

Together with features of the lifting suture 400 according to the fourth embodiment of the present invention, the lifting suture 600 according to the sixth embodiment of the present invention is featured in that after forming holes 620 in the fiber yarn 610, anchor part materials are preferably injected into the holes 620, thereby integrally forming the anchor parts 520 with the fiber yarn 510 in a closely packed manner.

In addition, sutures 700 and 800 according to seventh and eighth embodiments of the present invention are configured as shown in FIGS. 7 and 8, respectively.

The sutures 700 and 800 applied to the present invention include fixing parts 730 and 830 each formed at one side and fixable to the skin, and variable parts 740 and 840 each movably and fixably formed at the other side and laterally symmetrical with respect to the fixing parts 730 and 830, respectively.

Of course, only one among the fixing parts 730 and 830 and the variable parts 740 and 840 applied to the present invention can be formed at only one of opposite sides of each suture.

In addition, the fixing parts 730 and 830 and the variable parts 740 and 840 applied to the present invention are configured such that anchor parts 720 and 820 protruding on outer circumferences of the fiber yarns 710 and 810 are integrally formed with the fiber yarns 710 and 810 by a double injection, respectively.

In addition, the anchor parts 720 and 820 of the fixing parts 730 and 830 and the variable parts 740 and 840 applied to the present invention provide the lifting sutures in which the anchor parts 720 and 820 are formed one by one at regular intervals so as to expose the fiber yarns in regions where the anchor parts 720 and 820 are formed to the outside, respectively.

Meanwhile, the anchor parts 720 of the lifting suture 700 according to the seventh embodiment of the present invention are made of the same material with or a different material from the fiber yarn 710, wherein the anchor parts 720 include funnel-shaped, symmetric V-grooves integrally formed with the fiber yarn 710 at their first ends along the outer circumference of the fiber yarn 710 by a double injection to effectuate a locking operation.

In addition, the fiber yarn 710 of the lifting suture 700 according to the seventh embodiment of the present invention may be manufactured in form of a mesh. Here, the fixing parts 730 and the variable parts 740 of the lifting suture 700 are configured such that the anchor parts 720 protruding on the outer circumference of the fiber yarn 710 are integrally formed with the fiber yarn 710 by a double injection while injection-molding the fiber yarn 710 in form of a mesh. In addition, the anchor parts 720 of the fixing parts 730 and the variable parts 740 provide the lifting suture 700 in which the anchor parts 720 are formed one by one at regular intervals so as to expose the fiber yarn 710 to the outside.

Figure 7A:
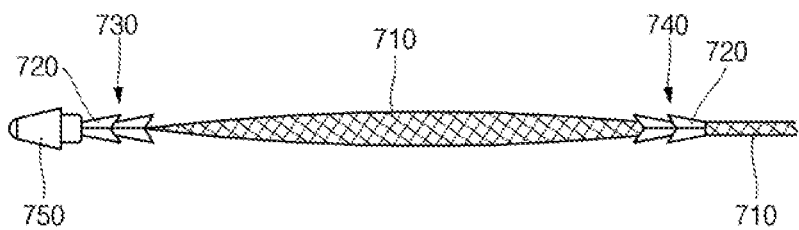
FIGS. 7A, 7B and 7C are a perspective view, a front view and a cross-sectional View of a lifting suture (700) according to a seventh embodiment of the present invention.

The lifting suture 700 shown in FIG. 7A may include a cover 750 formed at its one end. The cover 750 may be formed to correspond to an end of a needle (not shown) and a region coupled to the end of the suture 700. Like the biodegradable suture 700, the cover 750 may be made of a material that is degradable in the human body. In addition, the cover 750 is cone-shaped and functions as a guide for an insertion passageway when the needle and the suture 700 are inserted into the human body. In addition, the cone-shaped cover 750 may prevent the human body from being hurt when the needle and the suture 700 are inserted into the human body.

In addition, the anchor parts 820 of the lifting suture 800 according to the eighth embodiment of the present invention are made of the same material with or a different material from the fiber yarn 810, wherein the anchor parts 820 include funnel-shaped, symmetric V-grooves integrally formed with the fiber yarn 810 at their first ends along the outer circumference of the fiber yarn 810 by a double injection to effectuate a locking operation.

In addition, the lifting suture 800 according to the eighth embodiment of the present invention further includes a mesh connector part 860 covering the fiber yarn 810 between the fixing parts 830 and the variable parts 840. The mesh connector part 860 is formed in a mesh type by a double injection simultaneously when the anchor parts 820 protruding on the outer circumference of the fiber yarn 810 are integrally formed with the fiber yarn 810 by means of the fixing parts 830 and the variable parts 840 by the double injection.

Likewise, the anchor parts 820 of the fixing parts 830 and the variable parts 840 provide the lifting suture 800 in which the anchor parts 820 are formed one by one at regular intervals so as to expose the fiber yarn 810 to the outside.

In addition, like the lifting suture 700 shown in FIG. 7, the lifting suture 800 shown in FIG. 8 may also include a cover 850 formed at its one end. Since the cover 850 is the same with the cover 750 shown in FIG. 7, a detailed description will not be repeated.

Particularly, the anchor parts 120, 220, 320, 420, 520, 620, 720, and 820 applied to the present invention are preferably made of the same materials with or different materials from the fiber yarns 110, 210, 310, 410, 510, 610, 710, and 810, wherein the anchor parts 120, 220, 320, 420, 520, 620, 720, and 820 include funnel-shaped, symmetric V-grooves integrally formed with the fiber yarn 710 at their first ends along the outer circumferences of the fiber yarns 110, 210, 310, 410, 510, 610, 710, and 810, by a double injection to effectuate a locking operation, respectively.

Of course, the anchor parts may be formed in diverse shapes other than the V-groove shape.

In addition, according to the present invention, after forming the recesses 250 and 550 in the fiber yarns 210 and 510, anchor part materials are preferably injected into the recesses 250 and 550, thereby integrally forming the anchor parts 220 and 520 in a closely packed manner.

In addition, after forming the holes 260 and 66 in the fiber yarns 310 and 610, anchor part materials are preferably injected into the holes 260 and 660, thereby integrally forming the anchor parts 320 and 620 in a closely packed manner.

Additionally, the sutures 100, 200, 300, 400, 500, 600, 700, and 800 applied to the present invention are preferably made of a biodegradable polymer material that is hydrolyzed in the skin and then eliminated within a predetermined period.

Here, the biodegradable polymer material employed in the present invention is preferably one selected from the group consisting of poly lactic acid (PLA), polydioxanone (PDO) and polyglycolicacide (PGA).

The polylactic acid (PLA) is an environmentally friendly resin derived from a source material extracted from corn starch. Since no endocrine-disrupting chemicals or harmful materials, such as heavy metals, are detected from PLA, PLA-based products are safe even when used for packing hot food or when bitten or sucked by babies. Biodegradable PLA-based plastics in use may demonstrate features equivalent to those of general plastics. However, once the biodegradable plastics come into disuse, they can be completely biodegraded by microorganisms.

The polydioxanone (PDO) and the polyglycolicacide (PGA) have similar features to the PLA.

Operations and effects of the aforementioned lifting sutures according to the present invention and the manufacturing method therefor will now be described.

First, according to the present invention, fiber yarns and anchor parts of the lifting sutures are integrally formed by a double injection or by multiple injections of two or more of injection stages, thereby improving tensile strengths of the lifting sutures and forming the anchor parts in diverse shapes, which are illustrated in the accompanying drawings as follows.

Figure 1B:
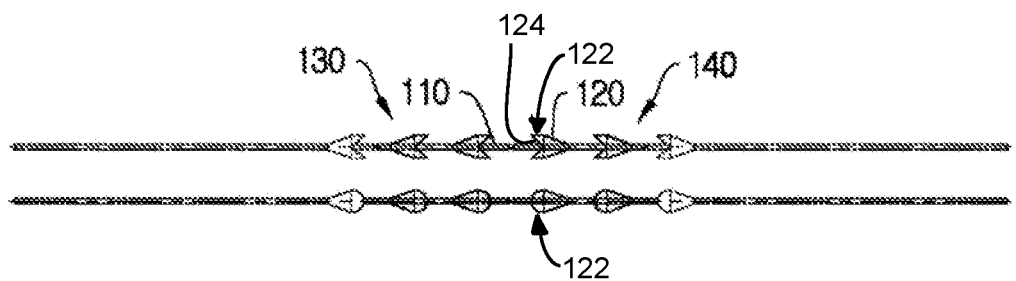
FIG. 1C is a cross-sectional view of the lifting suture 100 in the second orientation.
Figure 1C:
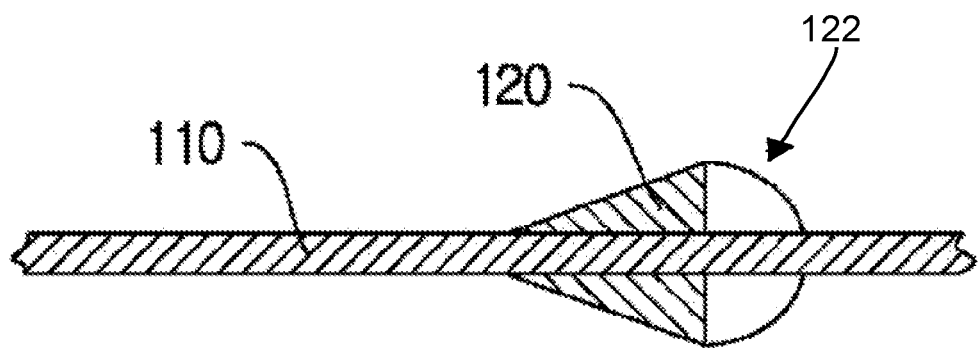

FIG. 1 shows the first embodiment of the lifting suture 100 applied to the present invention, including a perspective view (FIG. 1A), a front view (FIG. 1B), and a cross-sectional view (FIG. 1C).

Figure 2A:
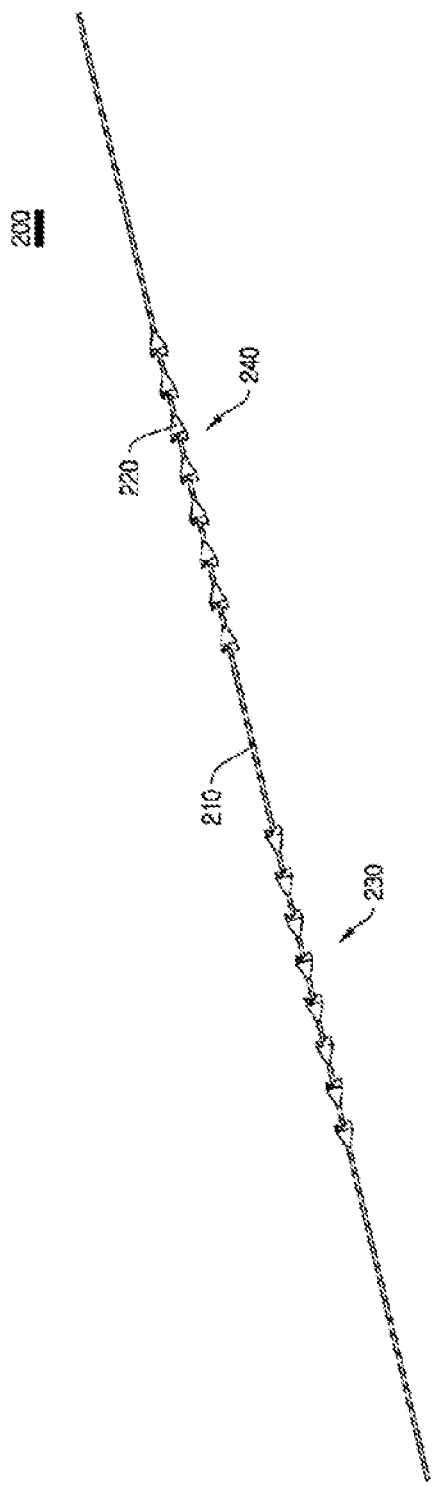
FIGS. 2A, 2B and 2C are a perspective view, a front view and a cross-sectional view of a lifting suture (200) according to a second embodiment of the present invention.
Figure 2B:
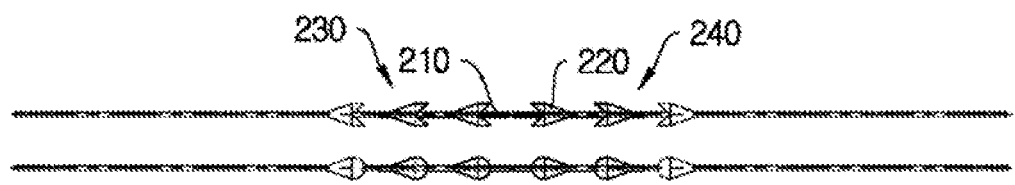
Figure 2C:
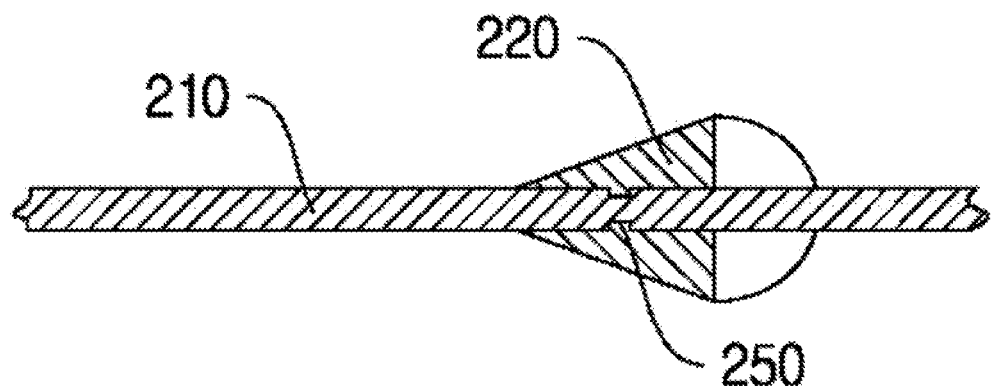

FIG. 2 shows the second embodiment of the lifting suture 200 applied to the present invention, including a perspective view (FIG. 2A), a front view (FIG. 2B), and a cross-sectional view (FIG. 2C).

Figure 3A:
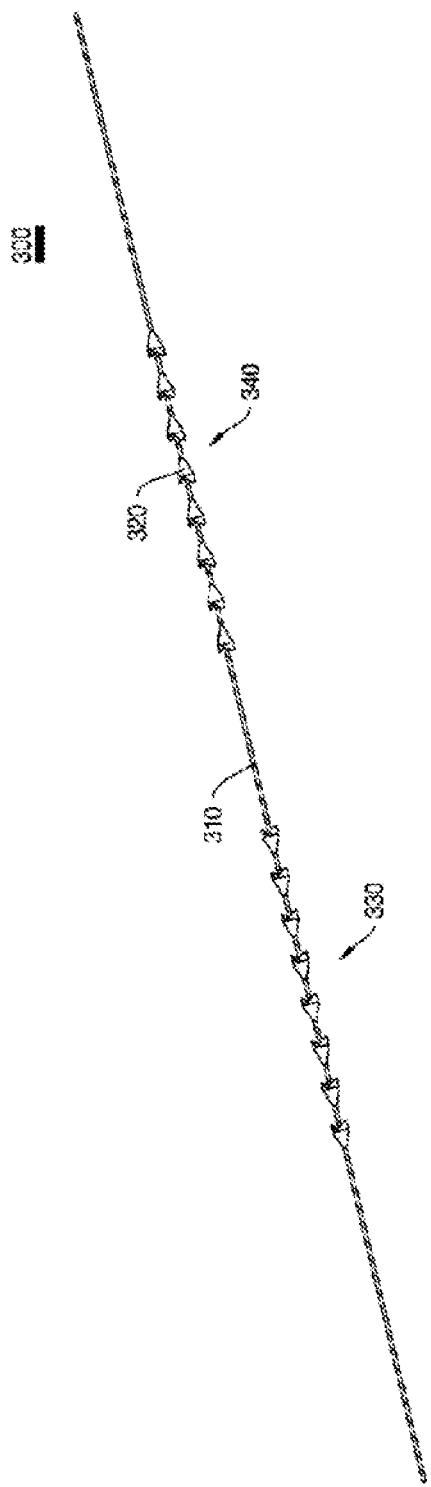
FIGS. 3A, 3B and 3C are a perspective view, a front view and a cross-sectional View of a lifting suture (300) according to a third embodiment of the present invention.
Figure 3B:
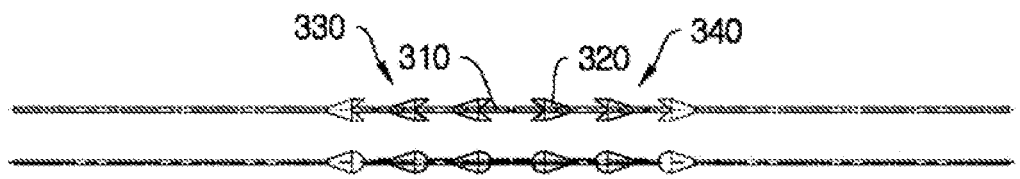
Figure 3C:
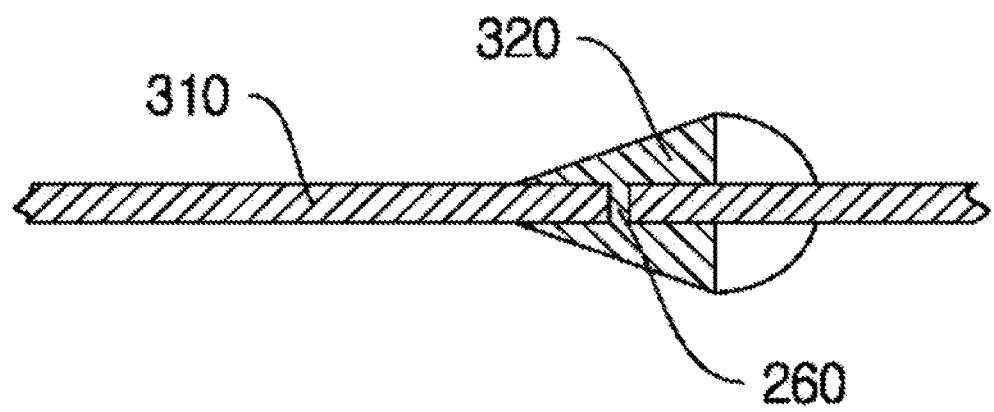

FIG. 3 shows the third embodiment of the lifting suture 300 applied to the present invention, including a perspective view (FIG. 3A), a front view (FIG. 3B), and a cross-sectional view (FIG. 3C).

Figure 4A:
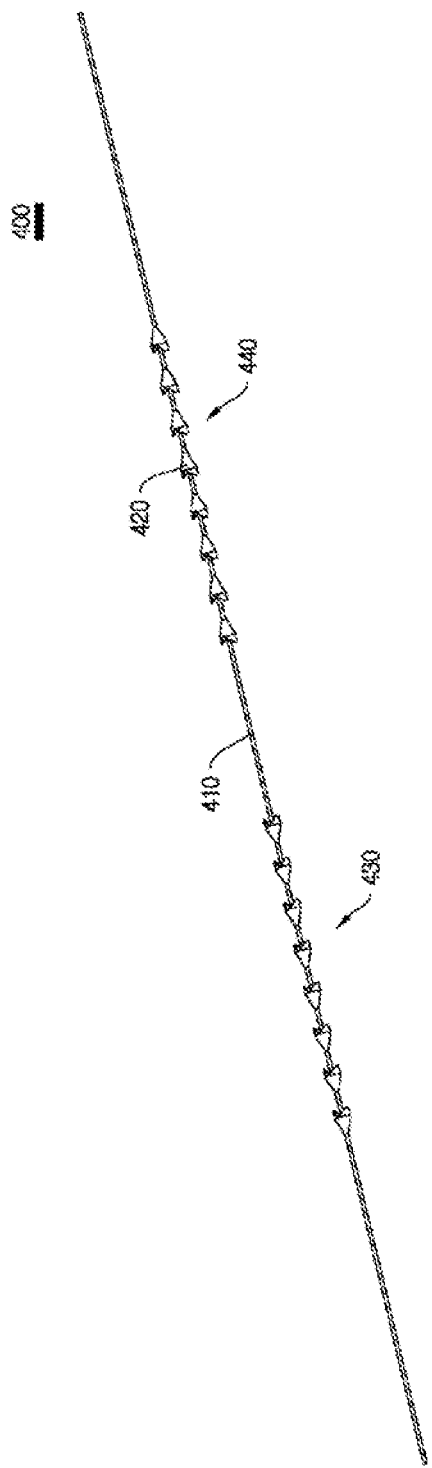
FIGS. 4A, 4B and 4C are a perspective view, a front view and a cross-sectional view of a lifting suture (400) according to a fourth embodiment of the present invention.
Figure 4B:
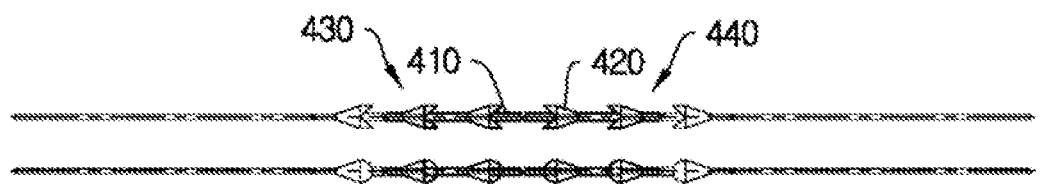
Figure 4C:
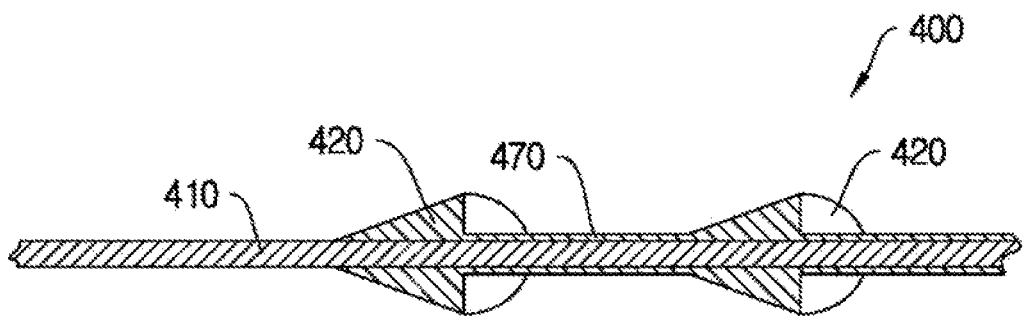

FIG. 4 shows the fourth embodiment of the lifting suture 400 applied to the present invention, including a perspective view (FIG. 4A), a front view (FIG. 4B), and a cross-sectional view (FIG. 4C).

Figure 5A:
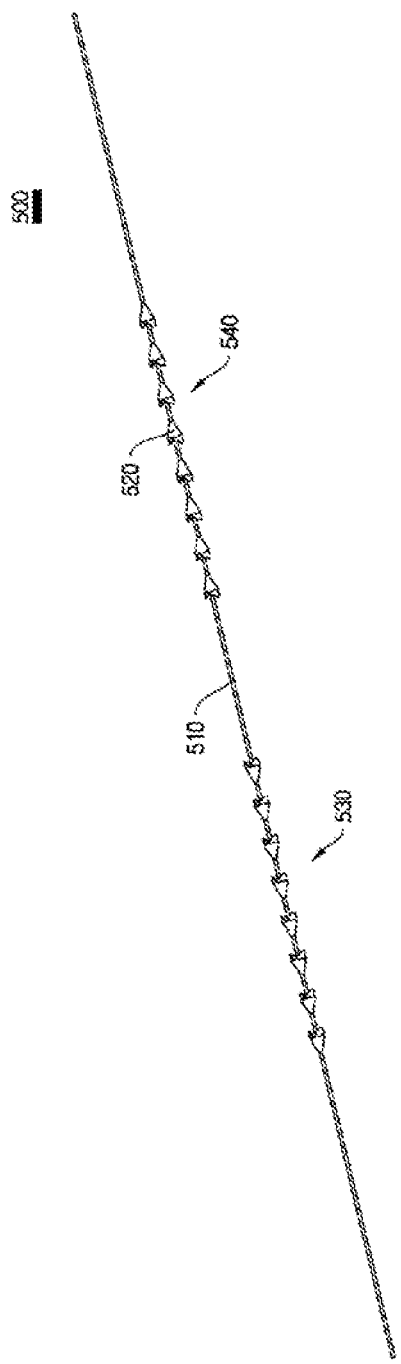
FIGS. 5A, 5B and 5C are a perspective view, a front view and a cross-sectional view of a lifting suture (500) according to a fifth embodiment of the present invention.
Figure 5B:
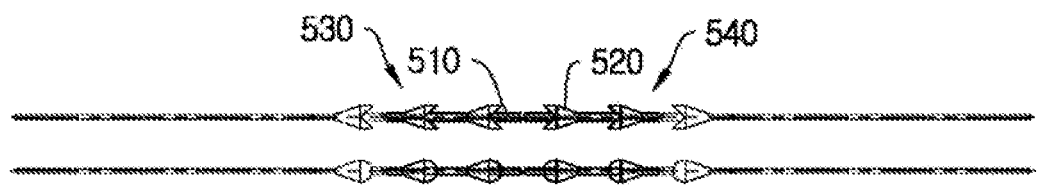
Figure 5C:
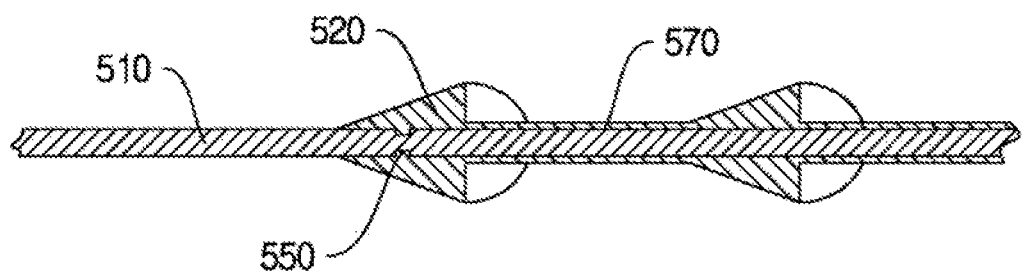

FIG. 5 shows the fifth embodiment of the lifting suture 500 applied to the present invention, including a perspective view (FIG. 5A), a front view (FIG. 5B), and a cross-sectional view (FIG. 5C).

Figure 6A:
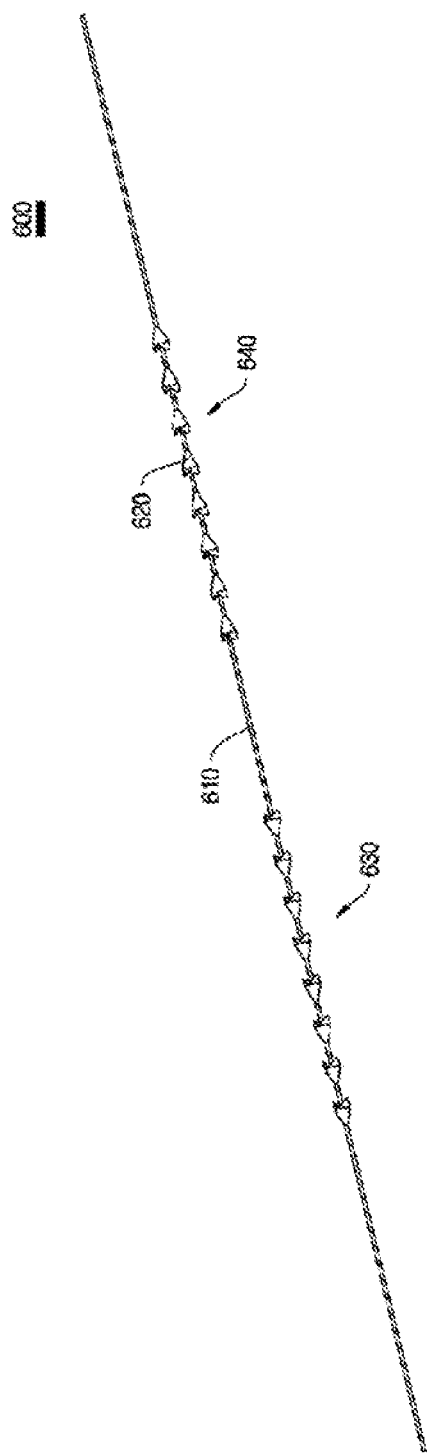
FIGS. 6A, 6B and 6C are a perspective view, a front view and a cross-sectional view of a lifting suture (600) according to a sixth embodiment of the present invention.
Figure 6B:
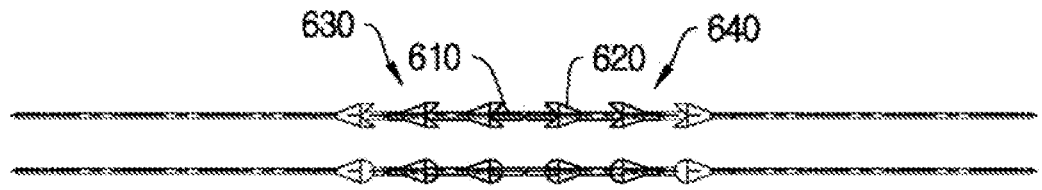
Figure 6C:
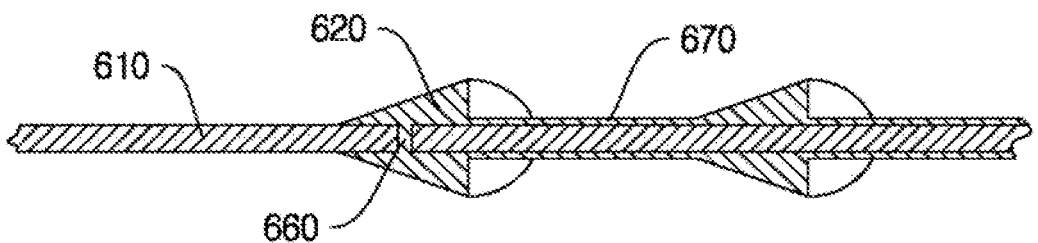

FIG. 6 shows the sixth embodiment of the lifting suture 600 applied to the present invention, including a perspective view (FIG. 6A), a front view (FIG. 6B), and a cross-sectional view (FIG. 6C).

Figure 7B:
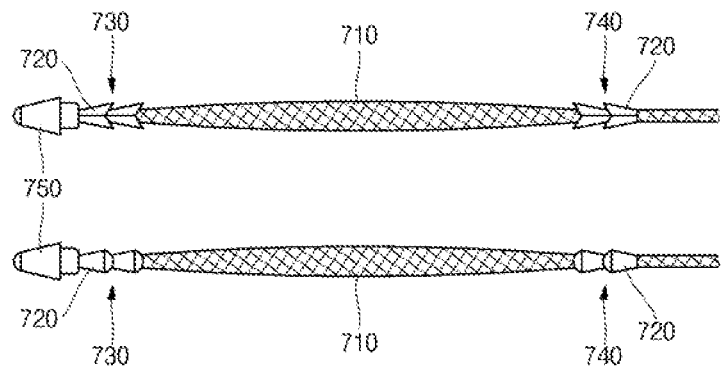
Figure 7C:
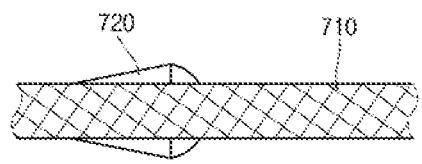

FIG. 7 shows the seventh embodiment of the lifting suture 700 applied to the present invention, including a perspective view (FIG. 7A), a front view (FIG. 7B), and a cross-sectional view (FIG. 7C).

Figure 8A:
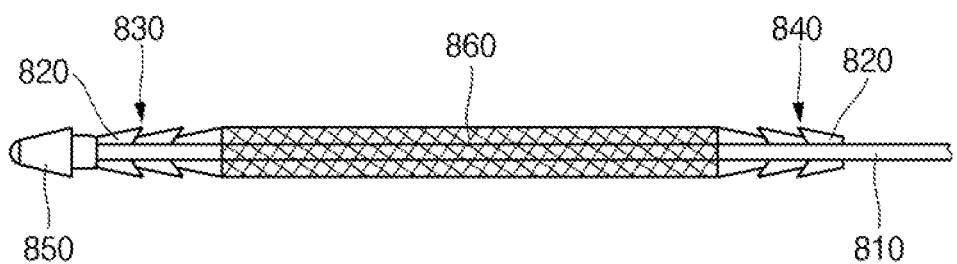
FIGS. 8A, 8B and 8C are a perspective view, a front view and a cross-sectional view of a lifting suture (800) according to an eighth embodiment of the present invention.
Figure 8B:
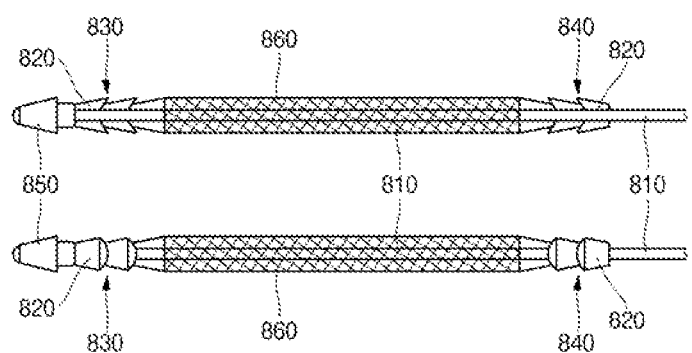
Figure 8C:
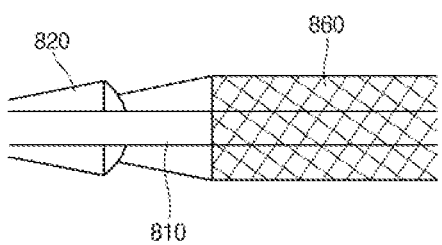

FIG. 8 shows the eighth embodiment of the lifting suture 800 applied to the present invention, including a perspective view (FIG. 8A), a front view (FIG. 8B), and a cross-sectional view (FIG. 8C).

The lifting sutures 100, 200 and 300 according to the first, second and third embodiments of the present invention are manufactured in the following manner. That is to say, the present invention provides a manufacturing method for the lifting sutures 100, 200 and 300 made of biodegradable polymer materials, the manufacturing method including a step of injecting materials of the fiber yarns 110, 210 and 310 and anchor parts 120, 220 and 320, which are the same with or different from each other, into two injection devices (not shown).

Thereafter, in the manufacturing method according to the present invention is performed a step of integrally forming the anchor parts 120, 220 and 320 protruding on the outer circumferences of the fiber yarns 110, 210 and 310 with the fiber yarns 110, 210 and 310 by performing one-time molding by a double injection, respectively.

In the double injection, the anchor parts 120, 220 and 320 of the fixing parts 130, 230 and 330 and the variable parts 140, 240 and 340 are formed one by one at regular intervals so as to expose the fiber yarns 110, 210 and 310 to the outside, thereby manufacturing the lifting sutures 100, 200 and 300.

Meanwhile, the lifting sutures 400, 500 and 600 according to the fourth, fifth and sixth embodiments of the present invention are manufactured in the following manner.

That is to say, the present invention provides a manufacturing method for the lifting sutures 400, 500 and 600 made of a biodegradable polymer material, the manufacturing method including a step of forming the recesses 550 or holes 660 in the fiber yarns 410, 510 and 610, respectively.

Then, in the manufacturing method of the present invention is performed a step of injecting the fiber yarn having the recesses 550 or the holes 660 formed therein into an injection device (not shown), and then injecting materials of the anchor parts 420, 520 and 620, which are the same with or different from the materials of the fiber yarns 410, 510 and 610, into the injection device.

Next, a step of injecting the materials of the anchor parts 420, 520 and 620 into the recesses 550 or the holes 660 is performed, thereby integrally forming the anchor parts 420, 520 and 620 by a double injection in a closely packed manner.

In the double injection, the anchor parts 420, 520 and 620 of the fixing parts 430, 530 and 630 and the variable parts 440, 540 and 640 are formed in bundles with neighboring anchor parts 420 at regular intervals by the connector parts 470, 570 and 670 so as not to expose the fiber yarns 410, 510, 610 to the outside.

The lifting sutures 700 and 800 according to the seventh and eighth embodiments of the present invention are manufactured in the following manner.

That is to say, the present invention provides a manufacturing method for the lifting sutures 700 and 800 made of biodegradable polymer materials, the manufacturing method including a step of injecting materials of the fiber yarns 710 and 810, the mesh connector part 850 and the and anchor parts 720 and 820, which are the same with or different from one another, into two injection devices (not shown).

Thereafter, in the manufacturing method of the present invention is performed a step of integrally forming the anchor parts 720 and 820 protruding on the outer circumferences of the fiber yarns 710 and 810 with the fiber yarns 710 and 810 and the mesh connector part 860 covering the fiber yarns 710 and 810 by performing one-time molding by a double injection, respectively.

In the double injection, the anchor parts 720 and 820 of the fixing parts 730 and 830 and the variable parts 740 and 840 are formed one by one at regular intervals so as to expose the fiber yarns 710 and 810 to the outside, thereby manufacturing the lifting sutures 700 and 800.

Meanwhile, the biodegradable polymer material employed in the present invention is used in manufacturing the suture for lifting including one selected from the group consisting of poly lactic acid (PLA), polydioxanone (PDO) and polyglycolicacide (PGA) or collagen having a cell regenerating effect and biocompatibility.

The suture according to the present invention can definitely solve processing problems with conventional fiber yarns, that is, maintenance of tensile strength and diversity of anchor shapes, by a double injection (simultaneous injection of anchor parts and fiber yarn).

In addition, the suture according to the present invention has enhanced flexibility by forming the fiber yarn or the mesh connector part covering the fiber yarn in a mesh type. In addition, the suture according to the present invention allows an autogenous material to easily gather by forming the fiber yarn or the mesh connector part covering the fiber yarn in a mesh type.

In addition, the lifting suture according to an embodiment of the present invention can be easily manufactured and can efficiently inject a medical fluid by forming the suture in a mesh type suture.

As described above, those of ordinary skill in the art will readily appreciate that the present invention may be embodied in different forms without departing from the spirit or essential features of the invention. Therefore, these embodiments should not be construed as limitations but should be set forth for illustrative purposes in all aspects. It should be appreciated that the scope of the present invention is defined by the appended claims, rather than the detailed description of the invention and all changes and modifications derived from the meanings, scope and equivalent concepts of the appended claims can be included in the scope of the invention.

INDUSTRIAL APPLICABILITY

The technical ideas of the lifting suture according to the present invention and the manufacturing method thereof can be repeatedly practiced to reach the same results. In particular, since technological development can be facilitated by implementing the present invention, which contributes to advances and development of the industry, the present invention is sufficiently worthy to be protected.

The invention claimed is:

1. A suture for lifting comprising:
    a medical fiber yarn; and
    fixing parts formed on one side of the fiber yarn, the fixing parts comprising anchor parts protruding from an outer circumference of the medical fiber yarn, wherein the anchor parts are integrally formed with the medical fiber yarn, and wherein each anchor part comprises a solid frusto-conical shaped portion having a wide end and a narrow end and a locking portion extending from the wide end, the locking portion being hollow and having a cylindrical shaped wall extending circumferentially around the wide end of the solid frustoconical shaped portion, the cylindrical shaped wall defining symmetrical diametrically opposed V-shaped grooves.

2. The suture of claim 1, wherein the fixing parts are formed on a first side of the fiber yarn and the anchor parts are a first set of anchor parts, and the suture further comprises:
    variable parts movably or fixably formed on a second side of the fiber yarn, wherein the variable parts are laterally symmetrical with the fixing parts relative to a center of a length of the yarn, wherein the variable parts include a second set of anchor parts protruding from the outer circumference of the fiber yarn, wherein the second set of anchor parts are integrally formed with the fiber yarn.

3. The suture of claim 1, wherein the anchor parts are integrally formed with the fiber yarn by a double injection of the fiber yarn to form the suture.

4. The suture of claim 1, wherein the anchor parts are formed one by one at regular intervals, and the fiber yarn is exposed in regions between the anchor parts.

5. The suture of claim 1, wherein the anchor parts are formed in bundles with adjacent anchor parts and a material of the anchor parts extends over the yarn between the anchor parts.

6. The suture of claim 1, wherein the fiber yarn is injection-molded that forms a mesh-type pattern.

7. The suture of claim 2, further comprising a mesh connector part injection-molded into a mesh type pattern, the mesh connector part connected between the anchor parts of the fixing parts and the anchor parts of the variable parts and also covering the fiber yarn.

8. The suture of claim 7, wherein the mesh connector part is integrally formed with the fiber yarn together with the anchor parts by a double injection of the medical fiber yarn.

9. The suture of claim 1, wherein the anchor parts are made of a material that is the same or different from a fiber yarn material.

10. The suture of claim 1, wherein the fiber yarn includes recesses located to correspond to the anchor parts, and the anchor parts are integrally formed by injecting an anchor part material into the recesses.

11. The suture of claim 1, wherein the fiber yarn includes orifices located to correspond with and to the anchor parts, and wherein the anchor parts are integrally formed by injecting an anchor part material into the orifices.

12. The suture of claim 1, wherein the suture comprises a biodegradable polymer material that is hydrolyzed in the skin and then eliminated within a predetermined period of time.

13. The suture of claim 12, wherein the biodegradable polymer material is one or more of any of the group selected from; polylactic acid (PLA), polydioxanone (PDO) and polyglycolicacide (PGA).

\* \* \* \* \*